United States Patent
Yu et al.

(10) Patent No.: US 10,610,736 B2
(45) Date of Patent: Apr. 7, 2020

(54) ELECTRIC WALKING ASSISTANCE DEVICE FOR FACILITATING GAIT ACTIVITY AND THE APPLICATION METHOD THEREOF

(71) Applicant: National Yang-Ming University, Taipei (TW)

(72) Inventors: Chung-Huang Yu, Taipei (TW); Ying-Chun Jheng, Taipei (TW)

(73) Assignee: NATIONAL YANG-MING UNIVERSITY, Taipei (TW)

(*) Notice: Subject to any disclaimer, the term of this patent is extended or adjusted under 35 U.S.C. 154(b) by 301 days.

(21) Appl. No.: 15/639,888

(22) Filed: Jun. 30, 2017

(65) Prior Publication Data
US 2018/0178065 A1   Jun. 28, 2018

(30) Foreign Application Priority Data
Dec. 23, 2016   (TW) .............................. 105143004 A

(51) Int. Cl.
| A63B 24/00 | (2006.01) |
|---|---|
| A61H 3/00 | (2006.01) |
| A63B 71/06 | (2006.01) |
| G09B 19/00 | (2006.01) |
| A61H 3/04 | (2006.01) |

(52) U.S. Cl.
CPC .......... *A63B 24/0075* (2013.01); *A61H 3/00* (2013.01); *A61H 3/04* (2013.01); *A63B 24/0006* (2013.01); *A63B 24/0062* (2013.01); *A63B 71/0622* (2013.01); *G09B 19/003* (2013.01); *A61H 2003/043* (2013.01); *A61H 2201/1207* (2013.01); *A61H 2201/5007* (2013.01); *A61H 2201/5043* (2013.01); *A61H 2201/5079* (2013.01); *A61H 2201/5097* (2013.01); *A63B 2071/0625* (2013.01); *A63B 2071/0655* (2013.01); *A63B 2220/17* (2013.01);
(Continued)

(58) Field of Classification Search
CPC ............ A63B 24/0075; A63B 24/0006; A63B 24/0062; A63B 71/0622; A63B 2071/0625; A63B 2071/0655; A63B 2220/17; A63B 2220/20; A63B 2220/56; A63B 2220/803; A61H 3/00; A61H 3/04; A61H 2003/043; A61H 2201/1207; A61H 2201/5007; A61H 2201/5043; A61H 2201/5079; A61H 2201/5097; G09B 19/003
See application file for complete search history.

(56) References Cited

U.S. PATENT DOCUMENTS

| 8,845,494 B2* | 9/2014 | Whitall .............. A63B 69/0028 482/54 |
| 9,782,659 B2* | 10/2017 | Yamazaki .......... A63B 71/0054 |
| 2017/0303849 A1* | 10/2017 | De Sapio .............. A61B 5/1117 |

* cited by examiner

*Primary Examiner* — Timothy A Musselman
(74) *Attorney, Agent, or Firm* — Muncy, Geissler, Olds & Lowe, P.C.

(57) ABSTRACT

An electric walking assistance device is provided. The electric walking assistance device comprises: a support member comprising at least one movable component; a user area where a user can stand, wherein the user area is a ground area adjacent to the support member. The electric walking assistance device further comprises at least one gait monitoring module and at least one gait assisting module, wherein the at least one gait monitoring module and the at least one gait assisting module are on the support member, the user's body, an arbitrary point within the detection range covering a range of user activities or any combinations thereof.

26 Claims, 3 Drawing Sheets

Figure 1:
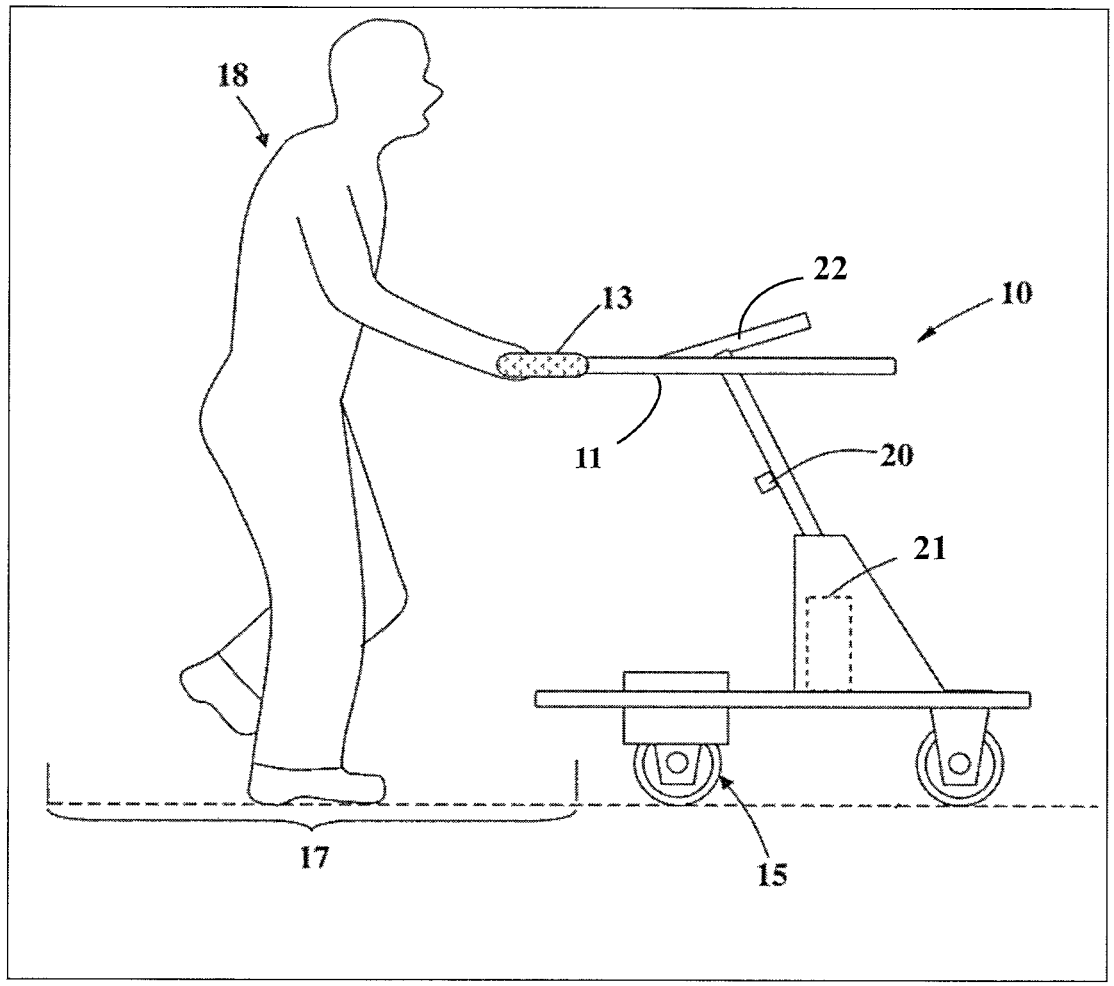

(52) U.S. Cl.
CPC ....... *A63B 2220/20* (2013.01); *A63B 2220/56* (2013.01); *A63B 2220/803* (2013.01)

ELECTRIC WALKING ASSISTANCE DEVICE FOR FACILITATING GAIT ACTIVITY AND THE APPLICATION METHOD THEREOF

CROSS-REFERENCE TO RELATED APPLICATION

Background of the Invention

Technical Field of the Invention

The present disclosure relates to an electric walking assistance device and an application thereof, and particularly to an electric walking assistance device for facilitating gait activity and an application thereof.

Background

A great demand for the quality walking assistance devices is increasing with the aging of population. Good walking assistance devices not only assist walking but also help the users to live more independently. In addition to assisting the users to overcome the problems of life, the safety and the convenience of the walking assistance devices in use are also important issues in developing the walking assistance devices. Accordingly, electric walking assistance devices may be basic needs in the future. Furthermore, electric walking assistance devices for fulfilling needs of different users is a future direction in development.

In general, the users of walking assistance devices can be categorized into two groups, one of which comprises those who need to rely on the walking assistance devices permanently, while the other comprises those who need to rely on the walking assistance devices temporarily. Specifically, the former group comprises seniors experiencing natural degeneration of their joints, patients comprising walking problems due to the neurologic diseases such as Parkinson's disease or patients who are weak due to diseases such as stroke. The latter group comprises people whose lower limbs are temporarily damaged by non-natural causes such as car accident or bedridden patients suffering from muscle atrophy. The requirements of the users for the walking assistance devices are different for different purposes.

Since the users who rely on the walking assistance devices temporarily still have good walking ability, the requirement for the walking assistance devices other than providing temporary assistance involves how to help the users resume normal walking after recovery. In particular, the user will walk with poor posture to reduce pain when the user's bones are not strong enough or when the muscles are not able to provide sufficient support, and such situation will weaken the user's joint stability, cause muscle imbalance or even cause secondary injury or lesion on the joint or muscle of the lower limb. As a result, the condition of the user after recovery may be even worse. Therefore, an ideal walking assistance device is an auxiliary walking device not only providing good support but also assisting the user to walk in the right way to enable the user to have good mobility without using the walking assistance device after recovery.

In addition, although the users who rely on the walking assistance devices permanently need to rely on the walking assistance devices for long term, the users can live more independently and without over-reliance on the assistance of others if they are able to continuously improve the walking ability with the walking assistance devices. Guiding the users in walking with most suitable gait pattern is a good way to improve the walking ability. Besides, strengthening the muscle groups involved in walking by using a walking assistance device and thus gradually reducing the reliance of the user on the walking assistance device is a better way another to improve the walking ability. In this way, patients can use walking assistance devices to accomplish more things, thus benefiting the user's physical and mental health.

In the current technical field related to the walking assistance devices, the walking assistance devices have been developed to notify the users in accordance with the schedule and thus served as tools for training the user's gait. However, the walking assistance devices cannot provide the most suitable notification for the user base on the user's real-time condition. In other words, when the user is unable to achieve scheduled progress due to strength or pain problem, the walking assistance devices as mentioned above will still continue to provide the user with notification, which the user is unable to achieve anymore. As a result, the gait training is not efficient.

Therefore, how to design a walking assistance device for facilitating gait activity not only acquiring the user's condition in real-time but also providing notification more suitable to the user's physical condition based on user feedback information is an important issue in this technical field.

SUMMARY OF INVENTION

The main object of the present disclosure is to provide an electric walking assistance device for facilitating gait activity by comprises an element capable of measuring the user's walking condition in real-time and provide the user with suitable presentation, feedback or notification when using the walking assistance device. Therefore, the electric walking assistance device improves the efficiency of the gait activity.

A further object of the present disclosure is to provide an electric walking assistance device for facilitating gait activity by comprising an element capable of inputting a desired value for training in advance. While using the electric walking assistance device, the electric walking assistance device measures the walking condition of the user to obtain real-time data, and then compares the real-time data with the target value. After calculating the difference between the real-time data and the target value, the walking assisting device will update and deliver the training notification to the user. Therefore, the electric walking assistance device improves the efficiency of the gait activity.

A further object of the present disclosure is to provide an electric walking assistance device for facilitating gait activity by comprising an element capable of providing the users with various types of visual, auditory and haptic feedback. The walking assistance device enables the user to conduct gait training in a correct posture by providing various forms of stimulation, thus improving the efficiency of the gait activity.

A further object of the present disclosure is to provide an application method of an electric walking assistance device for facilitating gait activity. The method is capable of obtaining the user's condition in real-time during the gait training, comparing the user's condition with an ideal condition or a preset condition of gait training, and providing notification for the user via hardware facilities to enable the user to correct the gait. Therefore, the application method improves the efficiency of the gait activity.

In order to achieve the object mentioned above, the present disclosure discloses an electric walking assistance device for facilitating gait activity. The electric walking assistance device comprises: a support member comprising at least one movable component; a user area where a user can stand, wherein the user area is a ground area adjacent to the support member. In addition, the electric walking assistance device further comprises at least one gait monitoring module and at least one gait assisting module, wherein the at least one gait monitoring module and the at least one gait assisting module are on the support member, the user's body, an arbitrary point within the detection range covering a range of user activities or any combinations thereof. The at least one gait monitoring module monitors the user's gait activity obtains at least one gait characteristic data via a monitoring means and can transmit the at least one gait characteristic data. The at least one gait assisting module can receive an instruction message and can provide the user with at least one notification based on the content of the instruction message. The notification can guide the user in gait training. In addition, the electric walking assistance device further comprises a control system provided on the support member. The control system is electrically connected or communicatively connected to both the at least one gait assisting module and the at least one gait monitoring module. The control system receives the at least one gait characteristic data transmitted by the at least one gait monitoring module, transforms the at least one gait characteristic data into the instruction message, and transmits the instruction message to the at least one gait assisting module.

In one embodiment of the present disclosure, a first target value is input to the control system in advance. After receiving the at least one gait characteristic data transmitted by the at least one gait monitoring module, the control system compares the at least one gait characteristic data with the first target value to obtain an error value, and then the control system carries out a calculation based on the error value to obtain a second target value. The second target value is transformed into the instruction message, and then the instruction message is transmitted to the at least one gait assisting module by the control system.

In one embodiment of the present disclosure, the at least one gait monitoring module comprises a an image acquisition module, an inertial measurement module, a somatosensory module, a distance measurement module, a distance scanning module, an angle measurement module, a pressure sensing module, a foot switch, or any combinations thereof.

In one embodiment of the present disclosure, the at least one gait characteristic data comprises stance phase duration, swing phase duration, double-limb support phase duration, the moment of heel strike, the moment of foot flat, the moment of heel off, the moment of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percent of the time of each stage in stance phase, or any combinations thereof.

In one embodiment of the present disclosure, the at least one gait assisting module comprises an audio gait assisting module, a haptic gait assisting module, a visual gait assisting module, or any combinations thereof.

In one embodiment of the invention, the audio gait assisting module comprises a speaker or an ear phone.

In one embodiment of the present disclosure, the haptic gait assisting module comprises electrical stimulation device, a vibration stimulation device, a device for light touch stimulation, a stroke stimulation device, a tapping stimulation device, a device for providing flow of air for stimulation, or a thermal stimulation device.

In one embodiment of the present disclosure, the visual gait assisting module comprises a projector device, an augmented reality device, a virtual reality device or a display device.

In one embodiment of the present disclosure, the at least one notification comprises a countdown sound, a beep sound, a voice, a change of pitch in a sound, occurrence frequency of sound, text, a color, an image, occurrence frequency of light, a change of the brightness of an image, vibration, electrical stimulation, a change in temperature, non-contact haptic sensation, a change in stimulation intensity, light touch, stroke, tapping, or any combinations thereof.

In addition, in order to achieve one of the objects as mentioned above, the present disclosure discloses an application method of the electric walking assistance device as mentioned above for facilitating gait activity. The method comprises steps of: monitoring the user, obtaining the at least one gait characteristic data of the user, and transmitting the at least one gait characteristic data to the control system by the at least one gait monitoring module; transforming the at least one gait characteristic data into the instruction message and transmitting the instruction message to the at least one gait assisting module by the control system; finally providing the user with the at least one notification based on the instruction message to assist the user in performing a gait activity by the at least one gait assisting module.

Furthermore, in order to achieve one of the objects of the present disclosure, the present disclosure also discloses an application method of the electric walking assistance device as mentioned above facilitating gait activity. The method comprises steps of: inputting a first target value into the control system; transmitting the first target value to the at least one gait assisting module by the control system; providing the user with at least one notification based on the first target value by the at least one gait assisting module to assist the user in performing a gait activity. While the user performs the gait activity, the at least one gait monitoring module monitors the user and obtains the at least one gait characteristic data of the user, and then the at least one gait monitoring module transmits the at least one gait characteristic data to the control system. The control system compares the at least one gait characteristic data with the first target value to obtain an error value after calculation, and then the control system carries out a calculation based on the error value to obtain a second target value. The second target value is transformed into the instruction message, and then the instruction message is transmitted to the at least one gait assisting module by the control system. Finally, the at least one gait assisting module provides the user with the at least one notification based on the instruction message to assist the user in performing the gait activity.

BREIF DESCRIPTION OF THE DRAWINGS

Figure 2:
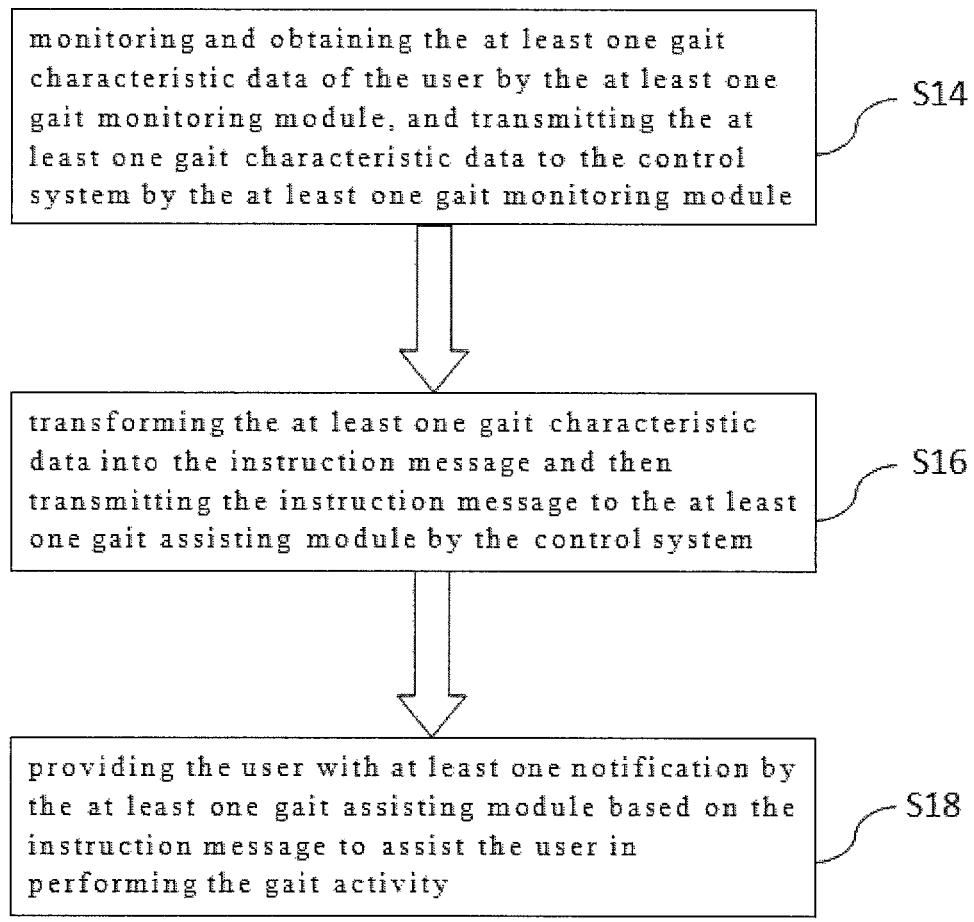
Figure 3:
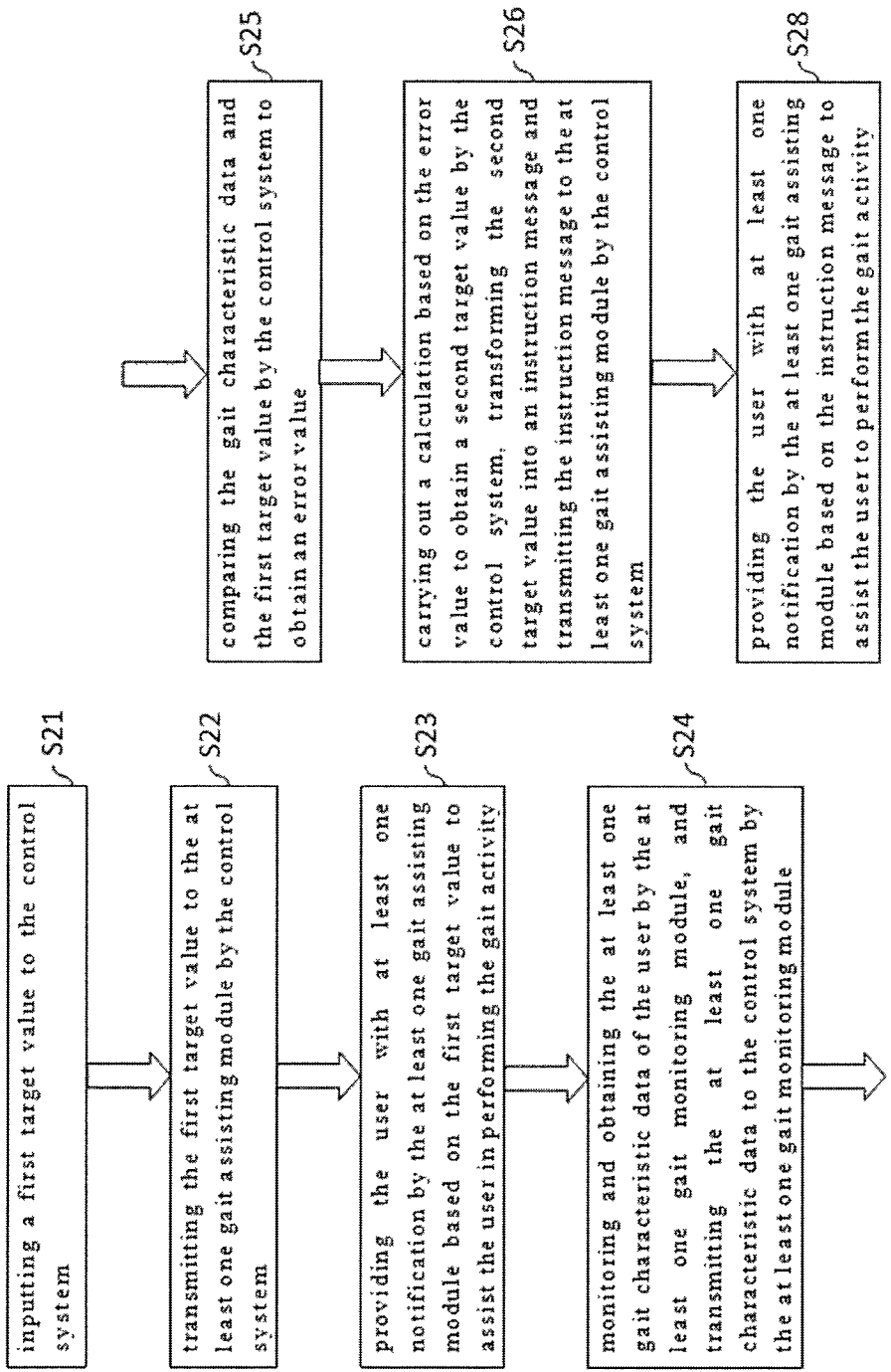

FIG. 1 is a schematic view of an electric walking assistance device for facilitating gait activity of a of a preferred embodiment in accordance with the present disclosure;

FIG. 2 is a s process flow diagram showing an application method of the electric walking assistance device for facilitating gait activity of a preferred embodiment in accordance with the present disclosure; and FIG. 3 is a process flow diagram showing an application method of the electric walking assistance device for facilitating gait activity of another preferred embodiment in accordance with the present disclosure.

DETAILED DESCRIPTION OF THE INVENTION

The detailed structure, operating principle and effects of the present disclosure will now be described in more detail hereinafter with reference to the accompanying drawings that show various embodiments of the present disclosure as follows.

In view of the fact that the conventional walking assistance devices cannot provide the most suitable notification to the user based on the user's real-time condition, which leads to an inefficient gait training, the present disclosure provides a novel electric walking assistance device for facilitating gait activity. By monitoring the user's real-time condition during usage of the walking assistance device, the electric walking assistance device of the present disclosure is able to dynamically adjust the content of the gait training for the user performing the gait activity so as to fulfill the user's need and to obtain the best result in training. In addition, the electric walking assistance device in accordance with present disclosure can also provide the user various types of visual, auditory and haptic feedback so as to offer various modes of training. As a result, the walking assistance device of the present disclosure enables the user to conduct gait training in a correct posture by providing various forms of stimulation, thus improving the efficiency of gait the activity.

Accordingly, the present disclosure provides an electric walking assistance device for facilitating gait activity. The electric walking assistance device comprises at least one gait monitoring module monitoring the user's real-time condition during walking to obtain related data as a reference for the system to analyze the user's gait information. Furthermore, the present disclosure also provides a control system not only receives and transforms the at least one gait characteristic data into an instruction message so as to instruct the at least one gait assisting module, but also compares the user data collected by the gait monitoring module with the ideal data input in the control system in advance so as to obtain an error value. The control system realizes the real-time condition of the user based on the error value and then provides the user with a notification to correct the user's gait and therefore reach the purpose of improving the efficiency of gait training. Lastly, the electric walking assistance device of the present disclosure provides at least one gait assisting module providing the users with various types of visual, auditory and haptic feedback so as to offer the user various modes of training. As a result, the walking assistance device of the present disclosure enables the user to conduct gait training in a correct posture by providing various forms of stimulation, thus improving the efficiency of the gait activity.

Reference will now be made in detail to the exemplary embodiments of the present disclosure, examples of which are illustrated in the accompanying drawings. Therefore, it is to be understood that the following is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this disclosure will be thorough and complete, and will fully convey the inventive concept to those skilled in the art. The relative proportions and ratios of elements in the drawings may be exaggerated or diminished in size for the sake of clarity and convenience in the drawings, and such arbitrary proportions are only illustrative and not limiting in any way. The same reference numbers are used in the drawings and the description to refer to the same or like parts. The properties, the functions and the mutual relations of the components of the modules will be described later, FIG. 1 is a schematic view of an electric walking assistance device for facilitating gait activity of a preferred embodiment in accordance with the present disclosure. Referring to FIG. 1, the electric walking assistance device comprises a support member 11. The support member 11 comprises at least one movable component 15 enables the support member 11 to move along the plane of progression. The support member 11 and a ground area adjacent to the support member 11 define a user area 17. A user can stand on the user area 17. In addition, the present disclosure also provides at least one gait monitoring module 20. The at least one gait monitoring module 20 monitors each detailed user information during the gait activity via a monitoring means and then transmits the at least one gait characteristic data to the control system 21 of the electric walking assistance device. The control system 21 is electrically connected or communicatively connected to the at least one gait assisting module 20. After the control system 21 receives the at least one gait characteristic data, the control system 21 can directly transform the gait characteristic data into the instruction message. Alternatively, after the control system 21 receives the at least one gait characteristic data, the control system 21 can compare the gait characteristic data with the first target value input in the control system in advance and then obtains an error value after calculation. A second target value is obtained based on the error value and then is transformed to an instruction message as well. Finally, the instruction message is transmitted to the at least one gait assisting module 22 electrically connected or communicatively connected to the control system 21. After the gait assisting module 22 receives the instruction message from the control system 21, the gait assisting module 22 provides the user a notification based on the content of the instruction message so as to guide the user in gait training to reach the training goal.

The support member 11 is for supporting the user and enabling the user to control his/her body when using the electric walking assistance device. The support member 11 helps the user to concentrate on the gait training or to assist the user in dealing with walking problem in daily life. In order to provide enough friction for the user while holding the support member 11, the support member 11 may further comprise a holder 13. Besides, the electric walking assistance device further comprises at least one movable component 15 configured on the support member 11. The movable component 15 enables the support member 11 to move more easily and smoothly along the plane of progression. The movable component 15 is electrically connected to the control system 21. Therefore, the movable component 15 can be either controlled by the user himself/herself or can be controlled by the control system 21 to move automatically. The movable component 15 comprises, but is not limited to, at least one wheel assembly, athey wheel assembly, or multiple roller assembly. Lastly, the support member 11 of the present disclosure and a ground area adjacent to the support member 11 define a user area 17. A user 18 can stand on the user area 17 and hold the support member 11 to perform the gait activity or gait training.

In addition, the support member 11 has sufficient space for installing the gait monitoring module 20, control system 22 or the gait assisting module 22 to reach the purpose of improving the efficiency of gait training while using the electric walking assistance device in accordance with the present disclosure. The properties, the functions and the mutual relations of the components of the modules will be described later.

Firstly, the at least one gait monitoring module 20 provided by the present disclosure can be configured on the support member 11, on the user's body 18, on an arbitrary point within the detection range covering a range of user activities or any combinations thereof. The at least one gait monitoring module monitors each detailed user information during the gait activity via a monitoring means, and the at least one gait monitoring module transmits the at least one gait characteristic data of the user 18 to the control system 21 for further calculation. By comprising the gait monitoring module 20, the electric walking assistance device 10 in accordance with the present disclosure is capable of observing the user's real-time condition during the gait training, and therefore providing a base for correcting the user's gait activity.

The gait activity is a periodic phenomenon of the user's physical characteristics during walking. The pattern of the normal gait shows that the two limbs move forward at distinctly separate times or bear the weight of the body, and one of the limbs maintains body balance when the other limb is moving forward to move in continuous smooth movements. The factors for determining whether the walking condition is smooth or not comprises the information about user's stride, gait cycle, step frequency, walking speed and weight bearing capacity of the foot etc. The walking condition of the user can be evaluated by one of the factors of a combination of multiple factors.

The term "stride", as used herein, is defined as the distance between two successive placements of the same foot. The stride reflects the symmetry and stability during the gait activity. In general, the users who depend on the walking assistance devices have shorter strides. The term "gait cycle", as used herein, is defined as the duration that occurs from the time when the heel of one foot contacts the ground to the time at which the same heel initially contacts the ground again. The gait cycle involves the stance phase, the swing phase and the double-limb support phase, etc. The stance phase occupies 60% of a normal gait cycle while the swing phase occupies 40% of a normal gait cycle. However, the people who rely on the walking assistance devices generally have longer stance phases and shorter swing phases. The term "step frequency, as used herein, is defined as number of steps per unit time. The step frequency reflects the gait tempo and is highly correlated with the velocity, which is the distance per unit time. The people who rely on the walking assistance devices generally have a slower step frequency and velocity. The term "weight bearing capacity of the foot', as used herein, is defined as the weight bearing on the foot during the double-limb support phase. The weight bearing capacity of the foot is closely related to the stability during the gait activity. The people who rely on the walking assistance devices generally have insufficient weight bearing capacity of the foot, which affects the balance and the rhythm during walking. Every factor mentioned above is an important indicator to evaluate the gait performance.

In order to accurately observe, define and determine the user's condition during the gait activity, the electric walking assistance device in accordance with the present disclosure provides the at least one gait characteristic data comprising stance phase duration, swing phase duration, double-limb support phase duration, the moment of heel strike, the moment of foot flat, the moment of heel off, the moment of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percent of the time of each stage in stance phase, or any combinations thereof. By providing various data from different approaches during the observation, the electric walking assistance device in accordance with the present disclosure can more accurately and objectively evaluate the user's condition. After the process of calculation and transformation executed by the control system 21, the electric walking assistance device can provide the user with the most suitable and immediate gait guidance. However, the gait characteristic data are not limited to the examples or descriptions provided. Any other suitable message sources can be employed within the scope of the present disclosure.

In general, the gait characteristic data is mainly based on foot force data such as weight-bearing position, the condition of transferring forces, and the pressure value, on time-related data such as the time required to move forward, swing time etc. and on spatial data such as joint angle, stride, etc. The condition during the entire gait activity cannot be completely observed if only a single type of gait monitoring module is used for measurement. As a result, in order to accurately obtain the gait characteristic data so as to comprehensively evaluate the user's condition during the gait activity, the electric walking assistance device in accordance with the present disclosure provides the gait monitoring module 20 comprising a combination of multiple monitoring devices with different principles so as to avoid missing any message beneficial for objectively analyzing the user's gait activity. For example, the gait monitoring module 20 can accurately measure the force data of each position on the foot sole and the weight bearing time by using mechanical type of monitoring module. For another example, the gait monitoring module 20 can observe the spatial gait parameters from step to step in the most direct way, indirectly obtaining the temporal parameters during each phase of the gait activity, and calculate each joint force of the limb during the gait activity. Accordingly, electric walking assistance device in accordance with the present disclosure provides the gait monitoring module 20 comprising an image acquisition module, an inertial measurement module, a somatosensory module, a distance measurement module, a distance scanning module, an angle measurement module, a pressure sensing module, a foot switch, or any combinations thereof. However, the gait monitoring module is not limited to the examples or descriptions provided. Any other suitable devices can be employed within the scope of the present disclosure.

Next, the present disclosure provides the at least one gait assisting module 22, which can be on the support member 11, the user's body 18, an arbitrary point within the detection range covering a range of user activities or any combinations thereof. The at least one gait assisting module 22 is electrically connected or communicatively connected to the control system 21 so as to receive the instruction message sent by the control system 21 and provide the user with at a notification based on the content of the instruction message. The notification can guide the user in gait training to reach the training goal.

The term "communicatively connected", as used herein, comprises connection methods for long-distance transmission of signals by wireless telecommunication, optical communication, acoustic communication, or electromagnetic induction. The connection methods can be performed by such as Wi-Fi, Bluetooth communication or wireless sensor network, etc. However, the method for wireless communication connection is not limited to the examples or descriptions provided.

The gait assisting module 22 provides the user with a notification by involving visual sensation, auditory sensation, and haptic sensation based on different parameters, such as stride, gait cycle, step frequency, walking speed and the weight bearing on the foot. Suitable notification is chose to carry out the corresponding gait guidance for gait training. For example, the gait assisting module 22 may assist the user to perform a walking activity with a suitable gait cycle by a notification with regular voice to assist the user in walking with a correct stride by light projection, or to ensure that the user provides sufficient weight on the foot during the stance phase by vibration feedback. With a variety of designs of sensory feedback for providing gait assistance, the present disclosure can provide the user with more different walking trainings and can evaluate the user's condition during the gait activity more comprehensively. According to the present principles, the present disclosure provides at least one notification comprising a countdown sound, a beep sound, a voice, a change of pitch in a sound, occurrence frequency of sound, text, a color, an image, occurrence frequency of light, a change of the brightness of an image, vibration, electrical stimulation, a change in temperature, non-contact haptic sensation, a change in stimulation intensity, light touch, stroke, tapping, or any combinations thereof.

Besides providing suitable notifications based on different parameters to provide gait assistance, the gait assisting module 22 provided by the present disclosure may also provide the user with multiple notifications based on the same parameter by involving visual sensation, auditory sensation, haptic sensation based on different parameters to provide gait assistance for training. For example, the gait assisting module 22 may simultaneously display a text notification on a display screen, send a voice notification to the ear phone which is wore by the user, and provide the user with vibration by the insole to show the user how to walk correctly. Therefore, the present disclosure reaches the purpose of improving the accuracy of gait training. By providing multiple notifications, the problem of delay of single notification, which leads to inconsistency between the user's movements and the desired movements, can be avoided or alleviated. The user can obtain different notifications providing different stimulation sensations in a single training so as to walk correctly during the gait training. Besides, when the bodily sensations receives the notifications showing the same desired movement, the user can be more concentrated on the training, thus improving the efficiency of the gait activity.

Accordingly, the present disclosure provides a gait assisting module 22 comprising an audio gait assisting module, a haptic gait assisting module, a visual gait assisting module, or any combinations thereof. The audio gait assisting module comprises a speaker or an ear phone. The haptic gait assisting module comprises electrical stimulation device, a vibration stimulation device, a device for light touch stimulation, a stroke stimulation device, a tapping stimulation device, a device for providing flow of air for stimulation, or a thermal stimulation device. The visual gait assisting module comprises a projector device, an augmented reality device, a virtual reality device or a display device. However, the gait assisting module is not limited to the examples or descriptions provided.

Lastly, the electric walking assistance device of the present disclosure also provides a control system 21. The control system 21 is on the support member 11 and is electrically connected to the movable component 15. Electrically connecting the movable component 11 and the control system 21 enables the control system 21 to control the movable component 15 based on the setting of the control system 21 and to further control the electric walking assistance device 10 to move based on the user's need. Besides, the control system 21 is electrically connected or communicatively connected to the at least one gait monitoring module 20. Therefore, the control system 21 can efficiently receive the gait characteristic data related to the gait activity of the user from the at least one gait monitoring module 20, and then transform the gait characteristic data or analyze and compare the gait characteristic data, and further transmits the gait characteristic data to the gait assisting module 22.

The control system 21 controls the movable component 15 either manually or automatically. Manual control can be carried out by the user inputting a normal gait value or a desired first target value to the control system 21 in advance, and the control system 21 then following the first target value to control the parameters such as the moving direction and the speed of the movable component 15 so as to reach the training goal. Automatic control can be carried out by the control system 21 being input a first target value in advance, and after the control system 21 receiving the gait characteristic data transmitted by the gait monitoring module 20 via electrical connection or communication connection, the control system 21 comparing and calculating the gait characteristic data and the first target value already in the control system 21 to obtain an error value, and the control system 21 generating a second target value based on the error value and then transforming the second target value into an instruction message to automatically control the parameters such as the moving direction and the speed of the movable component 15 so as to reach the purpose of dynamically adjust the user's training goal.

Similarly, the control system 21 controls the gait assisting module 22c in the same way as described above. After the user directly inputs a first target value, the control system 21 may follow the first target value to transmit an instruction message to the gait assisting module 22, and then the control system 21 may ask the gait assisting module 22 to provide at least one notification satisfying the first target value. In another example, after the gait monitoring module 20 obtains the gait characteristic data, the control system 21 may directly transform the target value or compare and adjust the target value and then transform the target value into an instruction message. The control system 21 may further ask the gait assisting module 22 to provide at least one notification satisfying the first target value to reach the purpose of dynamically adjust the user's training goal.

The method of the control system 21 performing a comparison and a calculation is described below. A normal gait value is saved in advance or a first target value is input in advance by the user based on his/her need or the instructions provided by the health care providers, and then the electric walking assistance device 10 is operated based on the first target value. During the operation, after the control system 21 receives the gait characteristic data transmitted from the at least one gait monitoring module 20, the control system 21 may compare the gait characteristic data and obtain basic parameters capable of evaluating the gait activity. The basic parameters comprises, for example, number of steps per minute, meters per second during walking, time for weight bearing, the amount of weight, or step length of every step. The control system 21 compares the value already saved in the control system 21 and determines the excess or insufficiency ratio of the value to the parameters for evaluating the gait activity so as to obtain an error value. A second target value is generated by evaluation of the error value, and then the second target value is transformed into an instruction message for asking the gait assisting module 22 to provide the user with at least one notification satisfying the second target value.

The instruction message provided by the present disclosure may be selected as a real-time instruction message or a target instruction message based on the need of the user. The term "real-time instruction message", as used herein, is defined as an instruction message directly feed backing to the user his/her gait condition monitored by the gait monitoring module. The real-time instruction message can enable the user to comprehensively realize his/her condition and then correct his/her posture according to the real-time instruction message. The term "target instruction message", as used herein, is defined as the instruction message that involves providing adjusted instruction based on the condition of the user monitored by the gait monitoring module. The adjusted instruction can be an adjustment transformed by specific ratio or an instruction message provided by the control system after comparison and adjustment. The instruction message can be transmitted to the gait assisting module to assist the user in correcting the gait, thus improving the efficiency of the gait activity.

The application method of the electric walking assistance device for facilitating gait activity may now be made in detail to the exemplary embodiments of the present disclosure. The properties, the functions and the mutual relations of the components of the modules will be described later.

FIG. 2 is process flow diagram showing an application method of the electric walking assistance device for facilitating gait activity of a preferred embodiment in accordance with the present disclosure. Referring to FIG. 2, the application method of the electric walking assistance device comprises steps of:

Step S14: monitoring and obtaining the at least one gait characteristic data of the user by the at least one gait monitoring module, and transmitting the at least one gait characteristic data to the control system by the at least one gait monitoring module;

Step S16: transforming the at least one gait characteristic data into the instruction message and then transmitting the instruction message to the at least one gait assisting module by the control system; and Step S18: providing the user with at least one notification by the at least one gait assisting module based on the instruction message to assist the user in performing the gait activity.

Referring to the Step S14 as shown in FIG. 2, the application method of the electric walking assistance device in accordance with the present disclosure can monitor the at least one gait characteristic data of the user by comprising the gait monitoring module so as to observe the user's condition in real time during the gait activity and transmit the least one gait characteristic data to the control system to provide sufficient information for the control system to carry out comparison and calculation.

The gait monitoring module is mainly based on the mechanical type of monitoring module and the optical type of monitoring module for monitoring the gait characteristic data comprising foot force data, the time-related data such as the time required to move forward, swing time etc., and the spatial data such as joint angle, stride, etc. The type and the number of the monitoring device in the gait monitoring module are not limited to one. By the gait monitoring module comprising a combination of multiple monitoring devices with different principles, not only the gait monitoring module improves the ability to analyze the user's gait activity, but also the control system enhances accuracy when performing the analysis and comparison of the signal. Accordingly, the present disclosure provides at least one gait monitoring module comprising an image acquisition module, an inertial measurement module, a somatosensory module, a distance measurement module, a distance scanning module, an angle measurement module, a pressure sensing module, a foot switch, or any combinations thereof.

The at least one gait characteristic data is the user's physical characteristic that is in a regular periodic manner. The at least one gait characteristic data comprises stride, gait cycle, step frequency, walking speed and weight bearing capacity, etc., all of which show the walking condition. To more accurately observe, define and determine the characteristic during the gait activity, the at least one gait characteristic data monitored by the present disclosure comprises stance phase duration, swing phase duration, double-limb support phase duration, the moment of heel strike, the moment of foot flat e, the moment of heel off, the moment of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percent of the time of each stage in stance phase, or any combinations thereof. By providing various data from different approaches during observation, the electric walking assistance device in accordance with the present disclosure can more accurately and objectively evaluate the user's condition during the gait activity. After the process of calculation and transformation executed by the control system 21, the electric walking assistance device can provide the user with the most suitable and immediate gait guidance. However, the gait characteristic data are not limited to the examples or descriptions provided. Any other suitable message sources can be employed within the scope of the present disclosure.

Referring to the Step S16 as shown in FIG. 2, during the application method of the electric walking assistance device in accordance with the present disclosure, after the control system receives the at least one gait characteristic data from the gait monitoring module, the control system can immediately transform the at least one gait characteristic data into an instruction message and then transmit to the at least one gait assisting module.

The instruction message in the present embodiment directly feedbacks to the user the condition during the gait activity, wherein the instruction message can be either positive feedback or negative feedback. The term "positive feedback", as used herein, is defined as the instruction message directly transmits the condition of the gait activity to the user without any discrepancy. For example, when the pressure sensing module begins to sense the pressure of the sole, the control system may provide the user with an instruction message by turning on the indicator light until the pressure sensing module no longer senses the pressure. The term "negative feedback", as used herein, is defined as instruction message blocking the notification of the electric walking assistance device originally provided for the user and enabling the user to realize the his/her own condition during gait activity by the length of time when the notification resuming from the blocking state. For example, the vibration device on the user provides the user with vibration notification during the swing phase constantly. When the pressure sensing module under the user's foot soles begins to sense no pressure, the control system may start to block the vibration form of instruction message until the user finishes the swing phase and the pressure sensing module senses the pressure again. If the user still feels the vibration after the swing phase, it means that the real swing phase of the user is shorter than the ideal swing phase. The user can decide whether to correct this situation or not.

The instruction message in the present embodiment may be selected as a real-time instruction message or a target instruction message based on the need of the user. The term "real-time instruction message", as used herein, is defined as an instruction message directly feed backing to the user his/her gait condition monitored by the gait monitoring module. The real-time instruction message enables the user to comprehensively realize his/her con condition and then correct his/her posture according to the real-time instruction message. The term "target instruction message", as used herein, is defined as the instruction message that involved providing adjusted instruction based on the condition of the user monitored by the gait monitoring module. The adjusted instruction can be an adjustment transformed by specific ratio. For example, during the gait activity, the target instruction message can show the user how to correct the gait activity to reach the target value. When the user reaches the target value, the target instruction message may show another target value higher than the previous one. The steps are repeated to challenge the user's limit till the user's gait performance becomes normal or till the user gives up correcting the gait.

Referring to the Step S18 as shown in FIG. 2, during the application method of the electric walking assistance device in accordance with the present disclosure, after the at least one gait assisting module receives the instruction message from the control system, the at least one gait assisting module can immediately provide the user with the at least on notification based on the instruction message so as to assist the user with gait activity. By then, the user can realize his/her condition during the gait activity by the content of the notification and evaluate if he/she need to correct the gait based on the notification.

The gait assisting module assists the user in gait activity mainly through visual sensation, auditory sensation, and haptic sensation. The gait assisting module can select a most suitable way of notification to assist the user in regard to different parameters or the gait assisting module can provide different notifications in regard to the same parameter for the user to perform the gait training, Accordingly, when the user receives the notifications from the gait assisting module and then conducts the gait training, the user may perform much more correctly in every detail during the gait activity. Besides, when the bodily sensations receives the notifications showing the same desired movement, the user can be more concentrated on the training, thus improving the efficiency of the gait activity.

Accordingly, the application method of the electric walking assistance device in accordance with the present disclosure assists the user by an audio gait assisting module, a haptic gait assisting module, a visual gait assisting module, or any combinations thereof. The audio gait assisting module comprises a speaker or an ear phone. The haptic gait assisting module comprises electrical stimulation device, a vibration stimulation device, a device for light touch stimulation, a stroke stimulation device, a tapping stimulation device, a device for providing flow of air for stimulation, or a thermal stimulation device. The visual gait assisting module comprises a projector device, an augmented reality device, a virtual reality device or a display device. The ways of providing a notification comprises a countdown sound, a beep sound, a voice, a change of pitch in a sound, occurrence frequency of sound, text, a color, an image, occurrence frequency of light, a change of the brightness of an image, vibration, electrical stimulation, a change in temperature, non-contact haptic sensation, a change in stimulation intensity, light touch, stroke, tapping, or any combinations thereof.

FIG. 3 is a process flow diagram showing an application method of the electric walking assistance device for facilitating gait activity of another preferred embodiment in accordance with the present disclosure. Referring to FIG. 3, the application method of the electric walking assistance device comprises steps of:

Step S21: inputting a first target value to the control system;

Step S22: transmitting the first target value to the at least one gait assisting module by the control system;

Step S23: providing the user with at least one notification by the at least one gait assisting module based on the first target value to assist the user in performing the gait activity;

Step S24: monitoring and obtaining the at least one gait characteristic data of the user by the at least one gait monitoring module, and transmitting the at least one gait characteristic data to the control system by the at least one gait monitoring module;

Step S25: comparing the gait characteristic data and the first target value by the control system to obtain an error value;

Step S26: carrying out a calculation based on the error value to obtain a second target value by the control system, transforming the second target value into an instruction message and transmitting the instruction message to the at least one gait assisting module by the control system; and Step S28: providing the user with at least one notification by the at least one gait assisting module based on the instruction message to assist the user to perform the gait activity.

The difference between the application method of the electric walking assistance device in accordance with the present embodiment and the previous embodiment is that in the present embodiment, the user inputs a target value in advance. After the conducts the gait activity by following the target value, the gait monitoring module may monitor the walking condition of the user and then transmit the walking condition to the control system to enable the control system to compare the walking condition and the target value and then make adjustment. Accordingly, the application method can provide a training mode more suitable for the user based on the walking condition, thus achieving the purpose of promoting gait activities.

As described in step S21, during the application method of the electric walking assistance device in accordance with the present embodiment, before the user uses the electric walking assistance device, the user can input a first target value into the control system in advance, wherein the first target value can be a normal gait value or a target value provided by the doctor or the user based on the rehabilitation progress or expectation, For example, a person with normal gait has a step frequency ranging from 90 to 120 steps per minute and a step length ranging from 35 cm to 40 cm, which the user in the later stages of rehabilitation can choose as the first target value to prepare for stopping relying on the walking assistance device.

As described in step S22, during the application method of the electric walking assistance device in accordance with the present embodiment, after the control system receives the first target value input by the user, the control system may immediately transform the first target value into the instruction message and then transmit the instruction message to the at least one gait assisting module. The instruction message is the same as the instruction message mentioned in the previous embodiment. The instruction message of the present embodiment is also a message directly instructs the gait assisting module what to do. For example, when the first target value is 100 steps pre minute, the instruction message can be an ear phone sending a sound with an occurrence frequency of 100 times per minute or can be a projector device sending a light with an occurrence frequency of 100 times per minute, depending on the type of gait assisting module the electric walking assistance device. The type, configuration and the function are substantially the same as that of the previous embodiment, and will not describe again herein.

As described in step S23, during the application method of the electric walking assistance device in accordance with the present embodiment, after the at least one gait assisting module receives the instruction message from the control system, the at least one gait assisting module may begin to provide the user with the at least one notification based on the content of the instruction message to assist the user in performing a gait activity, wherein the at least one notification is substantially the same as that of the previous embodiment, and will not describe again herein.

As described in step S24, during the application method of the electric walking assistance device in accordance with the present embodiment, the at least one gait monitoring module monitors and obtains the at least one gait characteristic data of the user and then transmits the at least one gait characteristic data to the control system, wherein the configurations and the functions of the at least one gait monitoring module and the control system are substantially the same as that of the previous embodiment, and the at least one gait characteristic data is substantially the same as that of the previous embodiment, and will not describe again herein.

As described in step S25, during the application method of the electric walking assistance device in accordance with the present embodiment, after the control system receives the gait characteristic data, the control system may first compare the gait characteristic data and the first target value input in advance as described in step S21 and then obtain an error value after calculation. The term "error value', as used herein, is defined as the difference between the real walking condition of the user and the expected walking condition. If the user's real walking condition is better than the first target value already input in the control system, the error value may be a positive value. If the user's real walking condition is worse than the first target value, the error value may be a negative value. The greater difference between the user's real condition and the first target value, the larger the absolute value of the error value. The error value may affect the way of subsequent adjustment.

As described in step S26, during the application method of the electric walking assistance device in accordance with the present embodiment, after the control system obtains the error value, the control system may obtain a second target value after calculation based on the error value and then transform the second target value into instruction message, which may be transmitted to the at least one gait assisting module, wherein the second target value is correlated to the error value. A non-obvious difference between the second target value and the absolute value of the error value shows that the user's real walking condition is close to the training goal. In such situation, the second target value can be the same as the first target value so as to enable the user to keep training to reach the original training goal. In another example, a positive value of the error value shows that the user is ahead of the rehabilitation schedule. In such situation, the second target value can be higher than the first target value so as to dynamically provide the user with another goal of rehabilitation. In another example, a negative value of the error value shows that the user's current walking condition cannot reach the expected training goal. In such situation, the second target value can be adjusted to a lower value, wherein the value is not limited to a fixed value. The second target value can be adjusted to a dynamical target value, which is gradually increased based on the user's walking condition. Therefore, the electric walking assistance device in accordance with the present disclosure reaches the purpose of improving the efficiency of gait training.

On the other hand, the second target value may similarly be a target value that is repeatedly adjusted and provided for the user. If the user reaches the target value, the target value may be adjusted to another target value higher than the current target value. The steps are repeated to challenge the user's limit till the user's gait performance becomes normal or till the user gives up correcting the gait. Finally, the control system transform the second target value into the instruction message and then transmits the instruction message to the at least one gait assisting module.

As described in step S28, during the application method of the electric walking assistance device in accordance with the present embodiment, the at least one gait assisting module provides the user with at least one notification after based on the instruction message to assist the user in performing a gait activity, wherein the configuration and the function of the at least one gait assisting module are substantially the same as that of the previous embodiment, and will not describe again herein.

In conclusion, the present disclosure provides an electric walking assistance device for facilitating gait activity and an application method thereof. The electric walking assistance device is capable of measuring every gait characteristic data of the user during the usage by comprising the at least one gait monitoring module. The gait characteristic data is further provided for the control system as a reference for calculation and analysis so as to enable the electric walking assistance device to fulfill the user's need. Besides, by comprising the control system, the electric walking assistance device can directly receive the message from the gait monitoring module and then feed back to the user. The control system can further compare the message with the first target value already input in the control system and then adjust the first target value based on the user's condition, thus improving the efficiency of the gait activity. Lastly, by comprising the multisensual gait assisting module, the electric walking assistance device enables the user to confirm that whether his/her movement is correct and enables the user to be highly concentrated on the training by providing multiple notifications. Accordingly, the electric walking assistance device enables the user to perform gait training with correct posture, thus improving the efficiency of the gait activity. Accordingly, the electric walking assistance device of the present disclosure has unexpected results compared to the conventional electric walking assistance device.

Hereinafter, it is to be understood that the following is illustrative of exemplary embodiments and is not to be construed as limited to the specific embodiments disclosed, and that modifications to the disclosed exemplary embodiments, as well as other exemplary embodiments, are intended to be included within the scope of the appended claims.

First Embodiment

Training on the Weight Bearing Status of the User by a Display Device Based on Visual Sensation The present embodiment provides an electric walking assistance device for facilitating gait activity. The electric walking assistance device comprises a support member comprising at least one movable component. The support member is electrically connected to a control system. The support member and a ground area adjacent to the support member define a user area where a user can stand. In addition, the electric walking assistance device for facilitating gait activity comprises a gait monitoring module comprising a pressure sensing module configured under the user's foot soles via communication connection. The electric walking assistance device further comprises another gait assisting module comprising a display device on the support member and electrically connected to the control system.

The user inputs a period of time of weight bearing status of the foot into the control system at the beginning. The control system displays an empty bar chart on the display device to show the period of time of weight bearing status of the foot input by the user. When the user starts a gait activity, the pressure sensing module on the user's insole may start to measure the period of time of weight bearing status of the foot during the stance phase and then the pressure sensing module may transmit the measurement result to the control system of the electric walking assistance device by communicative connection. The control system may dynamically show the process of the weight bearing status of the foot by such as filling the bar chart so as to enable the user to realize his/her weight bearing status of the foot. The control system may compare the measurement result with the period of time of weight bearing status of the foot already input in the control system at the same time and then obtain an error value. The control system may convert the error value into a target value, for example, the real measurement value +10 microseconds (μs). The control system may further transmit the target value to the display device. After display device receives the instruction message, the display device may adjust the bar chart to show the user the ideal period of time of weight bearing status of the foot during the stance phase, and the pressure sensing module may continuously provide the user the measurement result, The steps are repeated until the real-time data of the user's gait activity matches the ideal training value.

Second Embodiment

Training on the Weight Bearing Status of the User by a Sound Notification

The present embodiment provides an electric walking assistance device for facilitating gait activity. The electric walking assistance device comprises a support member comprising at least one movable component. The support member is electrically connected to a control system. The support member and a ground area adjacent to the support member define a user area where a user can stand. In addition, the electric walking assistance device for facilitating gait activity comprises a gait monitoring module comprising a pressure sensing module configured under the user's foot soles via communication connection. The electric walking assistance device further comprises another gait assisting module comprising an ear phone on the user and communicatively connected to the control system.

When the user starts to use the electric walking assistance device in accordance with the present disclosure, the pressure sensing module on the user's insole may start to measure the pressure value of the user's foot all the time and may transmit the measurement result to the control system of the electric walking assistance device by communicative connection. The control system transforms the pressure value measured by the pressure sensing module into a sound wave with different frequency based on the value of the pressure. When the pressure value is greater, the sound wave may have a higher frequency. The sound wave is then transmitted to the ear phone which is wore by the user via communication connection so as to enable the user to realize his/her weight bearing status of the foot during walking. The user may decide whether to correct the status or not based on the sound wave. When the user keeps performing the gait activity, the electric walking assistance device may also keep monitoring the user and keep providing data by the pressure sensing module. The steps are repeated until the real-time data of the user's gait activity matches the ideal training value.

Third Embodiment

Training on the Weight Bearing Status of the User by a Haptic Notification

The present embodiment provides an electric walking assistance device for facilitating gait activity. The electric walking assistance device comprises a support member comprising at least one movable component. The support member is electrically connected to a control system. The support member and a ground area adjacent to the support member define a user area where a user can stand. In addition, the electric walking assistance device for facilitating gait activity comprises a gait monitoring module comprising a pressure sensing module configured under the user's foot soles via communication connection. The electric walking assistance device further comprises another gait assisting module comprising a vibration wristband and a vibration insole both on the user and communicatively connected to the control system.

The user inputs an amount of weight bearing on the foot. When the When the user starts a gait activity, the pressure sensing module on the user's insole may start to measure the amount of weight bearing on the foot during the stance phase and then may transmit the measurement result to the control system of the electric walking assistance device by communicative connection. When the measurement result transmitted by the pressure sensing module and received by the control system reaches the amount of weight bearing on the foot already input in the control system, the control system may send a vibration signal to the user's insole and the wristband via communication connection. The vibration from the insole and the wristband enables the user to realize that his/her weight bearing status on the foot has reached the target value during walking and shows the user to move forward. The electric walking assistance device may also keep monitoring the user and keep providing data by the pressure sensing module. The steps are repeated until the real-time data of the user's gait activity matches the ideal training value.

Fourth Embodiment

Training on the Balance of the User During the Gait Activity by a Display Device Based on Visual Sensation The present embodiment provides an electric walking assistance device for facilitating gait activity. The electric walking assistance device comprises a support member comprising at least one movable component. The support member is electrically connected to a control system. The support member and a ground area adjacent to the support member define a user area where a user can stand. In addition, the electric walking assistance device for facilitating gait activity comprises a gait monitoring module comprising a somatosensory device configured via communication connection. The somatosensory device is configured on a point within the detection range covering a range of user activities. The electric walking assistance device further comprises another gait assisting module comprising a display device on the support member and electrically connected to the control system.

When the user starts a gait training, the somatosensory device configured on a point within the detection range covering a range of user activities may start to measure the period of the stance phase and the period of the swing phase and then the somatosensory device may transmit the measurement result to the control system of the electric walking assistance device by communicative connection. When the control system receives a heel-strike signal transmitted by the somatosensory device, the control system may start to instruct the display device of the electric walking assistance device to start a timer. When the control system receives a toe-off signal transmitted by the somatosensory device, the control system may instruct the display device to stop the timer. Therefore, the user can realize his/her walking condition. Meanwhile, after the control system receives the heel-strike signal and the toe-off signal of another foot transmitted by the somatosensory device, the control system may compare the signals with that of the other foot and then show the period of time between the adjacent heel strikes of the two to enable the user to realize each weight-bearing ratio on the two feet during walking and further realize his/her balance during the gait activity. The electric walking assistance device may also keep monitoring the user and keep providing data by the somatosensory device. The steps are repeated until the real-time data of the user's gait activity matches the ideal training value.

Fifth Embodiment

Training on the Weight Bearing Status of the User by a Sound Notification

The present embodiment provides an electric walking assistance device for facilitating gait activity. The electric walking assistance device comprises a support member comprising at least one movable component. The support member is electrically connected to a control system. The support member and a ground area adjacent to the support member define a user area where a user can stand. In addition, the electric walking assistance device for facilitating gait activity comprises a gait monitoring module comprising a pressure sensing module configured under the user's foot soles via communication connection. The electric walking assistance device further comprises another gait assisting module comprising an ear phone on the user and communicatively connected to the control system.

The user inputs two step frequency of the two feet separately at the beginning, and then sets up different seconds of the two feet contacting the ground based on the two step frequency separately, wherein the different seconds will be transmitted to the ear phone on the user. The ear phone may continually provide the user with a notification sound based on the seconds of the foot contacting the ground. When the user starts gait training, the pressure sensing module on the user's insole may start to measure the heel-strike signal and the toe-off signal and then transmit the measurement result to the control system of the electric walking assistance device by communicative connection. When the control system receives heel-strike signal, the control system may block and stop the notification sound from the ear phone until the control system receives the toe-off signal. Therefore, if the user still hears the notification sound for the right foot when he moves the right foot, it means that the period of time of weight bearing is too short and the step frequency is too high. When the total period of time of weight bearing exceeds the total seconds of the feet contacting the ground input in the control system at the beginning, the control system may transmit another notification sound to the ear phone to instruct the user to step forward. The electric walking assistance device keeps monitoring the user and keeps providing data by the pressure sensing module. The steps are repeated until the real-time data of the user's gait activity matches the ideal training value.

Sixth Embodiment

Training on the Step Frequency of the User by a Haptic Notification

The present embodiment provides an electric walking assistance device for facilitating gait activity. The electric walking assistance device comprises a support member comprising at least one movable component. The support member is electrically connected to a control system. The support member and a ground area adjacent to the support member define a user area where a user can stand. In addition, the electric walking assistance device for facilitating gait activity comprises a gait monitoring module comprising a pressure sensing module configured under the user's foot soles via communication connection. The electric walking assistance device further comprises another gait assisting module comprising a vibration wristband and a vibration insole both on the user and communicatively connected to the control system.

The user inputs two step frequency of the two feet separately at the beginning. When the user starts gait training, the control system may provide the user with a vibration notification via the vibration wristband or the vibration insole at the time when one of the feet needs to move forward to instruct the user to move forward. Meanwhile, the pressure sensing module on the user's insole starts to measure the heel-strike signal and the toe-off signal and then transmits the measurement result to the control system of the electric walking assistance device via communicative connection. The control system transforms the value measured by the pressure sensing module into a real step frequency and then compares the real step frequency with the step frequency input in the control system at the beginning to obtain an error value. The control system converts the error value into an instruction message indicating the vibration interval and then transmits the instruction message to the vibration wristband or the vibration insole. After the vibration wristband or the vibration insole receives the instruction message, the vibration wristband or the vibration insole may adjust the vibration interval so as to instruct the user when to move forward to maintain an ideal period of time of weight bearing during the stance phase. The steps are repeated until the real-time data of the user's gait activity matches the ideal training value.

Seventh Embodiment

Training on the Stride of the User by a Haptic Notification

The present embodiment provides an electric walking assistance device for facilitating gait activity. The electric walking assistance device comprises a support member comprising at least one movable component. The support member is electrically connected to a control system. The support member and a ground area adjacent to the support member define a user area where a user can stand. In addition, the electric walking assistance device for facilitating gait activity comprises a gait monitoring module comprising an image acquisition module configured on a point within the detection range covering a range of user activities via communication connection. The electric walking assistance device further comprises another gait assisting module comprising a projector device on the support member and electrically connected to the control system.

When the user starts gait training, the image acquisition module configured on a point within the detection range covering a range of user activities starts to measure the user's stride and then transmits the measurement result to the control system of the electric walking assistance device via communicative connection. When the control system receives the stride length of the user after a gait cycle, the control system may transmit an instruction message to the projector device. The projector device may project a baseline for correcting the step, a green area in front of the baseline, and a red are behind of the baseline so as to instruct and lead the user to move forward toward the baseline or toward the green area to improve the stride length. Furthermore, the control system keeps providing a target value beyond the user's ability during the gait activity by providing a target distance longer than the previous stride length by 20% in each gait cycle. Meanwhile, the projector device keeps instructing the user to adjust and correct the current gait activity to reach the target value. The process is repeated to challenge the user's limit till the user's gait performance becomes normal or till the user gives up correcting the gait. In the present embodiment a user can continuously adjust himself/herself and thus find a training goal most suitable for the user without the therapist's companion. Therefore, it is convenient for the user to perform the gait activity ay anywhere and anytime.

The foregoing description of preferred and other embodiments in the present disclosure is not intended to limit or restrict the scope or applicability of the inventive concepts conceived by the Applicant. In exchange for disclosing the inventive concepts contained herein, the Applicant desires all patent rights afforded by the appended claims. Therefore, it is intended that the appended claims include all modifications and alterations to the full extent that they come within the scope of the following claims or the equivalents thereof.

What is claimed is:

1. An electric walking assistance device for facilitating gait activity, comprising:
    a support member comprising at least one movable component, wherein the at least one movable component enables the support member to move horizontally;
    a user area where a user can stand, wherein the user area is a ground area adjacent to the support member;
    at least one gait monitoring module, wherein the at least one gait monitoring module is on the support member, the user's body, an arbitrary point within the detection range covering a range of user activities or any combinations thereof, and the at least one gait monitoring module obtains at least one gait characteristic data via a monitoring means and is capable of transmitting the at least one gait characteristic data;
    at least one gait assisting module, wherein the at least one gait monitoring module is on the support member, the user's body, an arbitrary point within the detection range covering a range of user activities or any combinations thereof, and the at least one gait assisting module is capable of receiving an instruction message and is capable of providing the user with at least one notification based on the content of the instruction message to assist the user in performing a gait activity; and
    a control system on the support member, wherein the control system is electrically connected or communicatively connected to both the at least one gait assisting module and the at least one gait monitoring module, and the control system receives the at least one gait characteristic data transmitted by the at least one gait monitoring module, transforms the at least one gait characteristic data into the instruction message, and transmits the instruction message to the at least one gait assisting module.

2. The electric walking assistance device for facilitating gait activity according to claim 1, wherein the control system is capable of being input a first target value in advance, comparing the at least one gait characteristic data with the first target value to obtain an error value after receiving the at least one gait characteristic data transmitted by the at least one gait monitoring module, carrying out a calculation based on the error value to obtain a second target value, transforming the second target value into the instruction message and transmitting the instruction message to the at least one gait assisting module.

3. The electric walking assistance device for facilitating gait activity according to claim 1, wherein the at least one gait monitoring module comprises an image acquisition module, an inertial measurement module, a somatosensory module, a distance measurement module, a distance scanning module, an angle measurement module, a pressure sensing module, a foot switch, or any combinations thereof.

4. The electric walking assistance device for facilitating gait activity according to claim 1, wherein the at least one gait characteristic data comprises stance phase duration, swing phase duration, double-limb support phase duration, the moment of heel strike, the moment of foot flat, the moment of heel off, the moment of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percent of the time of each stage in stance phase, or any combinations thereof.

5. The electric walking assistance device for facilitating gait activity according to claim 1, wherein the at least one gait assisting module comprises an audio gait assisting module, a haptic gait assisting module, a visual gait assisting module, or any combinations thereof.

6. The electric walking assistance device according to claim 5, wherein the audio gait assisting module comprises a speaker or an ear phone.

7. The electric walking assistance device for facilitating gait activity according to claim 5, wherein the haptic gait assisting module comprises electrical stimulation device, a vibration stimulation device, a device for light touch stimulation, a stroke stimulation device, a tapping stimulation device, a device for providing flow of air for stimulation, or a thermal stimulation device.

8. The electric walking assistance device for facilitating gait activity according to claim 5, wherein the visual gait assisting module comprises a projector device, an augmented reality device, a virtual reality device or a display device.

9. The electric walking assistance device for facilitating gait activity according to claim 1, wherein the at least one notification comprises a countdown sound, a beep sound, a voice, a change of pitch in a sound, occurrence frequency of sound, text, a color, an image, occurrence frequency of light, a change of the brightness of an image, vibration, electrical stimulation, a change in temperature, non-contact haptic sensation, a change in stimulation intensity, light touch, stroke, tapping, or any combinations thereof.

10. An application method of the electric walking assistance device for facilitating gait activity according to claim 1, comprising steps of:
monitoring the user, obtaining the at least one gait characteristic data of the user, and transmitting the at least one gait characteristic data to the control system by the at least one gait monitoring module;
transforming the at least one gait characteristic data into the instruction message and transmitting the instruction message to the at least one gait assisting module by the control system; and
providing the user with the at least one notification based on the instruction message to assist the user in performing a gait activity by the at least one gait assisting module.

11. The application method of the electric walking assistance device according to claim 10, wherein the instruction message is a real-time instruction message or a target instruction message.

12. The application method of the electric walking assistance device according to claim 10, wherein the at least one gait monitoring module comprises an image acquisition module, an inertial measurement module, a somatosensory module, a distance measurement module, a distance scanning module, an angle measurement module, a pressure sensing module, a foot switch, or any combinations thereof.

13. The application method of the electric walking assistance device according to claim 10, wherein the at least one gait characteristic data comprises stance phase duration, swing phase duration, double-limb support phase duration, the moment of heel strike, the moment of foot flat, the moment of heel off, the moment of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percent of the time of each stage in stance phase, or any combinations thereof.

14. The application method of the electric walking assistance device according to claim 10, wherein the at least one gait assisting module comprises an audio gait assisting module, a haptic gait assisting module, a visual gait assisting module, or any combinations thereof.

15. The application method of the electric walking assistance device according to claim 14, wherein the audio gait assisting module comprises a speaker or an ear phone.

16. The application method of the electric walking assistance device according to claim 14, wherein the haptic gait assisting module comprises electrical stimulation device, a vibration stimulation device, a device for light touch stimulation, a stroke stimulation device, a tapping stimulation device, a device for providing flow of air for stimulation, or a thermal stimulation device.

17. The application method of the electric walking assistance device according to claim 14, wherein the visual gait assisting module comprises a projector device, an augmented reality device, a virtual reality device or a display device.

18. The application method of the electric walking assistance device according to claim 10, wherein the at least one notification comprises a countdown sound, a beep sound, a voice, a change of pitch in a sound, occurrence frequency of sound, text, a color, an image, occurrence frequency of light, a change of the brightness of an image, vibration, electrical stimulation, a change in temperature, non-contact haptic sensation, a change in stimulation intensity, light touch, stroke, tapping, or any combinations thereof.

19. An application method of the electric walking assistance device for facilitating gait activity according to claim 2, comprising steps of:
inputting a first target value into the control system;
transmitting the first target value to the at least one gait assisting module by the control system;
providing the user with at least one notification based on the first target value by the at least one gait assisting module to assist the user in performing a gait activity;
monitoring the user and obtaining the at least one gait characteristic data of the user by the at least one gait monitoring module, and transmitting the at least one gait characteristic data to the control system by the at least one gait monitoring module;
comparing the at least one gait characteristic data with the first target value to obtain an error value after calculation by the control system;
carrying out a calculation based on the error value to obtain a second target value, transforming the second target value into the instruction message and transmitting the instruction message to the at least one gait assisting module by the control system; and
providing the user with the at least one notification based on the instruction message by the at least one gait monitoring module to assist the user in performing the gait activity.

20. The application method of the electric walking assistance device according to claim 19, wherein the at least one gait monitoring module comprises an image acquisition module, an inertial measurement module, a somatosensory module, a distance measurement module, a distance scanning module, an angle measurement module, a pressure sensing module, a foot switch, or any combinations thereof.

21. The application method of the electric walking assistance device according to claim 19, wherein the at least one gait characteristic data comprises stance phase duration, swing phase duration, double-limb support phase duration, the moment of heel strike, the moment of foot flat, the moment of heel off, the moment of toe off, foot strikes, hip angle, knee joint angle, hip joint position, ankle angle, number of steps per unit time, walking distance per unit time, step length of the healthy side, step length of the affected side, stride length, step width, foot angle, gait symmetry, change in balance, body alignment, base of support, ratio of the stance phase to the swing phase on the same side, ratio of the stance phase to the swing phase on the different sides, percent of the time of each stage in stance phase, or any combinations thereof.

22. The application method of the electric walking assistance device according to claim 19, wherein the at least one gait assisting module comprises an audio gait assisting module, a haptic gait assisting module, a visual gait assisting module, or any combinations thereof.

23. The application method of the electric walking assistance device according to claim 22, wherein the audio gait assisting module comprises a speaker or an ear phone.

24. The application method of the electric walking assistance device according to claim 22, wherein the haptic gait assisting module comprises electrical stimulation device, a vibration stimulation device, a device for light touch stimulation, a stroke stimulation device, a tapping stimulation device, a device for providing flow of air for stimulation, or a thermal stimulation device.

25. The application method of the electric walking assistance device according to claim 22, wherein the visual gait assisting module comprises a projector device, an augmented reality device, a virtual reality device or a display device.

26. The application method of the electric walking assistance device according to claim 19, wherein the at least one notification comprises a countdown sound, a beep sound, a voice, a change of pitch in a sound, occurrence frequency of sound, text, a color, an image, occurrence frequency of light, a change of the brightness of an image, vibration, electrical stimulation, a change in temperature, non-contact haptic sensation, a change in stimulation intensity, light touch, stroke, tapping, or any combinations thereof.

* * * * *